USO05514652A

United States Patent [19]
Watanuki et al.

[11] Patent Number: 5,514,652
[45] Date of Patent: May 7, 1996

[54] THERAPY OF RESPIRATORY TRACT DISEASES USING BASIC FIBROBLAST GROWTH FACTOR

[75] Inventors: Mitsuru Watanuki; Tsutomu Nakamura; Masaru Ogawa, all of Kyoto, Japan

[73] Assignee: Kaken Pharmaceutical Co., Ltd., Japan

[21] Appl. No.: 122,521

[22] PCT Filed: Feb. 15, 1993

[86] PCT No.: PCT/JP93/00189

§ 371 Date: Oct. 22, 1993

§ 102(e) Date: Oct. 22, 1993

[87] PCT Pub. No.: WO93/15753

PCT Pub. Date: Aug. 19, 1993

[30] Foreign Application Priority Data

Feb. 14, 1992 [JP] Japan ........................ 4-59549

[51] Int. Cl.$^6$ ........................ A61K 38/18; C12N 15/00
[52] U.S. Cl. ........................ 514/12; 530/399; 435/69.1; 435/69.4; 514/826
[58] Field of Search ................ 530/399; 514/12; 435/69.1, 69.4

[56] References Cited

U.S. PATENT DOCUMENTS

| | | | |
|---|---|---|---|
| 4,956,455 | 9/1990 | Esch et al. | 530/399 |
| 4,994,559 | 2/1991 | Moscatelli et al. | 530/399 |
| 5,006,343 | 4/1991 | Benson et al. | 424/450 |

OTHER PUBLICATIONS

Albes et al *The Annals of Thoraeic Surgery*, 57(2):444–449 (1994).

Basilico et al *Adv. Cancer Res* 59:115–165 (1992).

Bejin et al *Chest* 95(4):842–849 (1989).

Cormier et al *Chest* 104(4):1038–1042 (1993).

Henke et al *America J. of Pathology* 143(4):1189–1199 (1993).

Lemaire et al *Am. Review of Resp. Diseases* 134(4):653–658 (1986).

Thornton et al. *Clin Exp Immunol* 90:447–452 (1992).

Primary Examiner—Marianne P. Allen
Assistant Examiner—Karen E. Brown
Attorney, Agent, or Firm—Graham & James

[57] ABSTRACT

The present invention relates to a preparation for the therapy of respiratory tract diseases which contains a basic fibroblast growth factor and/or a homologue thereof as an active ingredient, a preparation for the therapy of respiratory tract diseases which contains a human basic fibroblast growth factor and/or a homologue thereof, produced by microorganisms or cultured cells prepared by genetic recombination, as an active ingredient, and a method for the therapy of respiratory tract diseases by administering any one of these preparations.

3 Claims, 4 Drawing Sheets

THERAPY OF RESPIRATORY TRACT DISEASES USING BASIC FIBROBLAST GROWTH FACTOR

TECHNICAL FIELD

The present invention relates to a preparation the therapy of respiratory tract diseases, used for the therapy of allergic and anallergic respiratory tract diseases or respiratory tract or bronchial tube impairments caused by the inhalation of respiratory tract impairing substances such as acids.

TECHNICAL BACKGROUND

For the therapy of respiratory tract diseases such as allergic or anallengic asthma or chronic or acute bronchitis, a xanthine derivative, a βsympathetic nerve acceptor stimulating preparation and an anticholine preparation are used as a bronchial tube dilating preparation. These preparations ape used in various forms such as a tablet, a powder, granules, a suppository, syrup, an intravenous solution, a hypodermic solution, an intramuscular preparation and an inhalant. The preparation form is selected from these depending upon the disease graveness and age of a patient.

Further, for the therapy of the above diseases at an intermediate or higher graveness level in particular, a steroidal drug having anti-inflammatory activity is used. This drug is known to have not only anti-inflammatory activity but also a therapeutical effect on the incompetent state of a βacceptor. This drug is mainly intravenously administered at present, while it is recently being emphasized that this drug has efficacy when administered by inhalation.

An anti-allergic drug is used as a drug for preventing respiratory tract diseases such as allergic asthma or chronic or acute bronchitis. This drug exhibits its effect by inhibiting the antagonistic activity to mediators such as histamine and leucotriene and the release of the mediators from mast cells.

Preparations according to Chinese medicine such as *Ephedrea herba*, *Bupleuri radix* and a fluid therapy agent are recently used alone or in combination for the therapy of the above diseases. Further, there are used specific therapies using allergenic extracts and a nonspecific alterative treatment agent using a gold preparation, bacterial vaccine and histamine-added γ-globulin although the mechanism of the latter for producing an effect has not yet been made clear.

Respiratory tract diseases caused by a respiratory system disease are therapeutically treated depending upon the diseases. For example, in infectious diseases, an antibiotic is administered in addition to the above drugs.

In respiratory tract diseases (injury) caused by the inhalation of an acid or an organic solvent or by the inhalation of hot air, not only autotherapy is expected but also an anti-inflammatory preparation such as a steroidal drug or an antibiotic against a possible infectious disease is used.

A basic fibroblast proliferation factor (also called a basic fibroblast growth factor, to be referred to as "bFGF" hereinafter) is a peptidyl cell growth factor which has been recognized to be present in the pituitary, brain, retina, corpus luteum, adrenal, kidney, placenta, prostate, thymus, chondrosarcoma and macrophage of a human being and other specific mammals (Cell Growth Factor, Part II, compiled by Japanese Tissue Culture Society, Asakura Publishing Co.). In the beginning, it has been found that bFGF exhibits high proliferation activity in a fibroblast such as BALB/c3T3 (D. Gospondarowicz: Nature 249: 123, 1974), and it was named such due to this activity. Then, it has been also found that it promotes the proliferation of almost all cells from amesoderm, particularly an endothelial cell (D. Gospondarowicz: National Cancer Institute Monograph 48: 109, 1978) and also promotes the proliferation of satellite cells of skeletal muscle (R. E. Allen: Exp. Cell Res. 152: 154, 1984).

Further, the clinical application of bFGF to various diseases is being studied recently. For example, bFGF is clinically applied to the therapy of wound, and bFGF is also clinically applied to the restoration of a blood vessel using its vascularization activity.

Moreover, a fibroblast-derived epithelial growth factor has been recently found, and it may be therefore inferred that the production of the fibroblast-derived epithelial growth factor is increased since bFGF activates the fibroblast.

On the other hand, in the field of the therapy of respiratory tract diseases, studies of asthma and chronic or acute bronchitis are vigorously under way. In the studies, an inflammation reaction of a respiratory tract caused by inflammatory cells induced or allowed to infiltrate by various stimulants is studied in close-up, and impairments of a respiratory tract and bronchial epithelial cells and peeling of epithelial cells caused by the impairments attract attention as symptoms. It is therefore a drug having the promotion activity for restoring an impaired epithelial portion that is being desired as a therapeutical drug.

The present invention has been made in view of the above therapies and therapeutical studies of respiratory tract diseases. It is an object of the present invention to provide a novel preparation for the therapy of respiratory tract diseases, which can alleviate respiratory tract hypersensitivity and prevent respiratory tract diseases From becoming intractable or permit the therapy of intractable respiratory tract diseases by restoring that portion of a respiratory tract or bronchial tube where the epithelial cells are impaired or peeled, observed in respiratory tract diseases.

DISCLOSURE OF THE INVENTION

In the therapy of respiratory tract diseases and the above trend of studies of bFGF, the present inventors have diligent studies to achieve the above object. As a result, the present inventors have found for the first time that the respiratory tract hypersensitivity of respiratory tract diseases can be alleviated, respiratory tract diseases can be prevented from becoming intractable and intractable respiratory tract diseases can be therapeutically treated by the administration of bFGF for the proliferation, or promotion of proliferation, of bronchial epithelial cells in a diseased part. And, the present inventors have succeeded in developing a drug useful as one for the therapy of respiratory tract diseases such as asthma and chronic or acute bronchitis, and have arrived at the present invention.

PREFERRED EMBODIMENTS OF THE INVENTION

Figure 1:
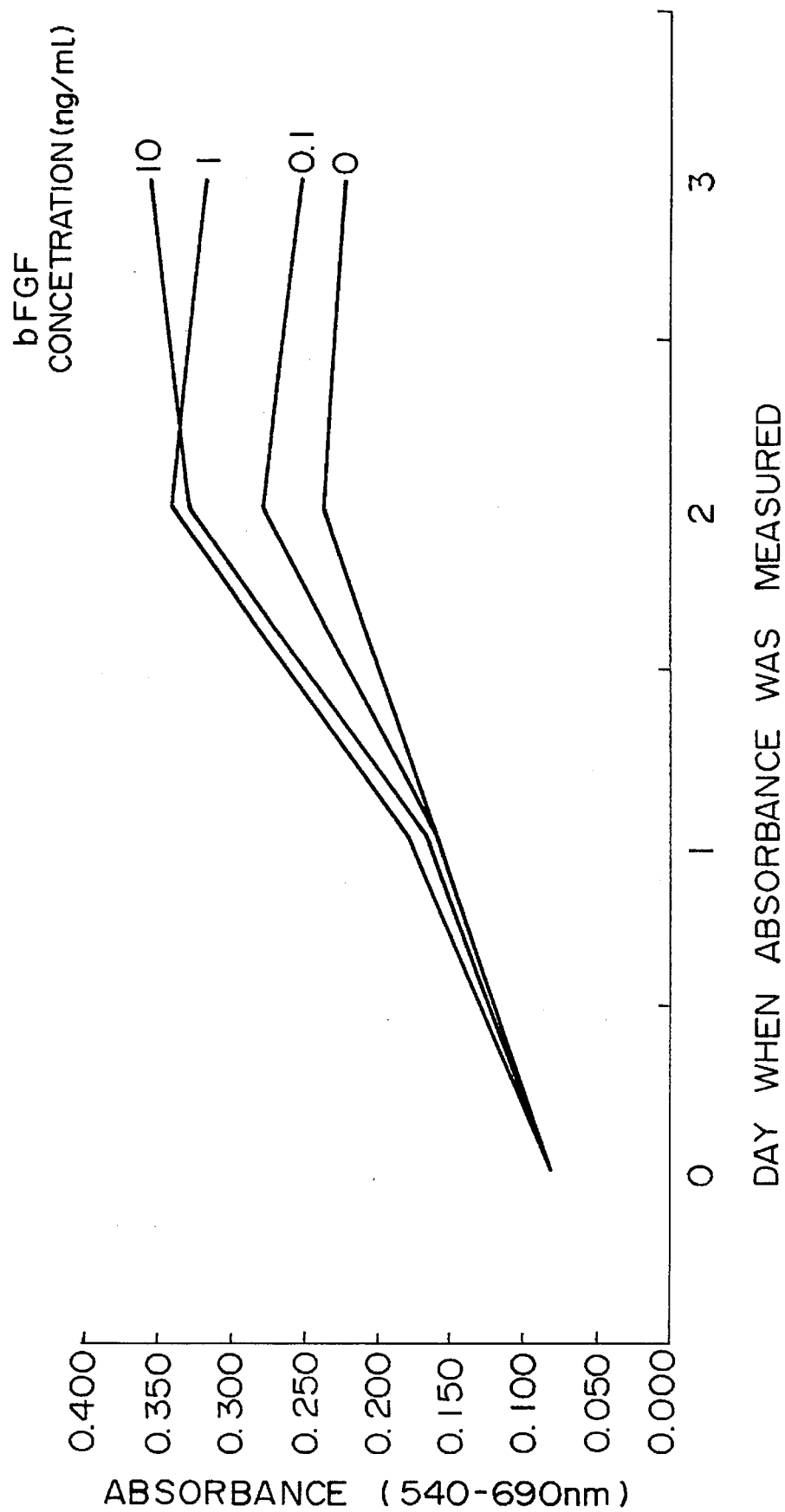
FIG. 1 is a graph showing the activity of bFGF for the proliferation promotion in Example 1 to be described later.

The present invention will be explained in detail hereinafter.

bFGF which is an active ingredient in the preparation for the therapy of respiratory tract diseases, provided by the present invention, is a known growth factor as described above, and its existence is recognized in a human being, a bovine, a mouse and a rat. In any one of these animals, bFGF basically shows the same activity to a living body. For applying the preparation for the therapy of respiratory tract diseases, provided by the present invention, to a human body, it is particularly preferred to use bFGF (to be referred to as "human bFGF" hereinafter) having the same amino acid sequence as that of bFGF produced in a human body in view of antigenicity.

Further, the preparation for the therapy of respiratory tract diseases, provided by the present invention, may contain a bFGF homologue as an active ingredient in place of bFGF itself. The bFGF homologue includes the following polypeptides (1) and (2).

(1) All of polypeptides which have substantially the same amino acid sequence as that of bFGF produced in specific mammals. The "substantially the same amino acid sequence" means that a polypeptide has an amino acid sequence of which 1 to 6 amino acid moieties are replaced with other different amino acids, but has the bioactivity of bFGF.

(2) All of polypeptides in which a segment of an additional amino moiety is added to the N-terminal and/or C-terminal of bFGF produced in specific mammals or to the N-terminal and/or C-terminal of the polypeptides described in the above (1), and which have the bioactivity of bFGF or the polypeptides described in the above (1).

In addition, the amount of bFGF present in a living body is very small. For industrially stably supplying the preparation for the therapy of respiratory tract diseases, provided by the present invention, it is therefore particularly preferred to use bFGF which microorganisms such as *Escherichia coli* or cultured cells are allowed to produce by genetic recombination technology or homologues thereof. When a gene for producing bFGF or its homologue (generally a polypeptide included in the above (1)) is inserted in a microorganism or a cultured cell, in general, the microorganism or cultured cell produces a polypeptide in which an additional amino acid segment is added to the N-terminal and/or C-terminal of bFGF or to the N-terminal and/or C-terminal of a polypeptide included in the above (1), i.e., a polypeptide included in the above (2).

Human bFGF is a polypeptide composed of 146 amino acids. For the preparation for the therapy of respiratory tract diseases, provided by the present invention, for example, a polypeptide composed of 146 amino acids, described in PCT Laid-open Publication No. 2-504468 (PCT W080/04832), may be used as a homologue included in the above (1), obtained by genetic recombination of human bFGF. In this polypeptide, each of cysteine (Cys) at 69-position and cysteine (Cys) at 87-position which constitute an amino acid sequence of human bFGF is replaced with serine (Ser).

A polypeptide composed of 155 amino acids, described in PCT Laid-open Patent Publication No. 63-500843 (PCT W087/01728), may be used as a homologue included in the above (2). This polypeptide is one in which a segment composed of 9 amino acids is added to the N-terminal of human bFGF.

Further, there may be used a polypeptide having Met- (methionine) in the N-terminal and composed of 147 amino acids, a polypeptide of 154 amino acids in which a segment composed of 8 amino acids is added to the N-terminal of bFGF, and a polypeptide having a segment composed of 11 amino acids added to the N-terminal and composed of 157 amino acids, described in PCT Laid-open Publication No. 63-501953 (PCT W087/03885).

In the preparation for the therapy of respiratory tract diseases, provided by the present invention, bFGF and its homologues may be used alone or in combination. Further, bFGF and/or its homologues alone may be used as an active ingredient alone, or may contain other drug.

The preparation For the therapy of respiratory tract diseases, provided by the present invention, is a drug containing the above bFGF and/or any one of its homologues as active ingredient(s). Specific examples of the form of the preparation include a solution containing bFGF and/or any one of its homologues and either a saline solution of other pharmacologically acceptable auxiliary (glucose, sucrose, buffer solution, heparin, hyaluronic acid and its salt, and collagen), an ointment containing this a solution, an inhalant, a solution for spray, a solution for injection, a gel prepared by the gelation of the above solution, and a fine powder. The preparation for the therapy of respiratory tract diseases, provided by the present invention, may be in any one of the forms of a systemic administration preparation and a topical administration preparation. In particular, however, topical administration is preferred since side effects are lower in topical administration than in systemic administration.

Preferred preparation examples are as follows.

[Preparation Example 1] Solution

| | |
|---|---|
| bFGF | 100 µg |
| Citric acid.monohydrate | 7.8 mg |
| Sodium citrate.dihydrate | 18.5 mg |
| EDTA.2Na.dihydrate | 3.72 mg |
| NaCl | 900 mg |
| Distilled water for injection | proper amount |
| Total amount | 10 ml |

[Preparation Example 2] Inhalant

| | |
|---|---|
| bFGF | 100 µg |
| Citric acid.monohydrate | 7.8 mg |
| Sodium citrate.dihydrate | 18.5 mg |
| EDTA.2Na.dihydrate | 3.72 g |
| Sodium chondoroitin sulfate | 500 mg |
| NaCl | 900 mg |
| Distilled water for injection | proper amount |
| Total amount | 10 ml |

[Preparation Example 3] Ointment

| | |
|---|---|
| bFGF | 1 mg |
| Collagen | 10 mg |
| Liquid paraffin | 0.2 g |
| White petrolatum | 0.7 g |
| PBS | proper amount |
| Total amount | 1 g |

[Preparation Example 4] Solution for injection

| | |
|---|---|
| bFGF | 100 µg |
| Hydroxyapatie | 10 mg |
| Distilled water for injection | proper amount |
| Total amount | 10 ml |

Examples of diseases to which the preparation for the therapy of respiratory tract diseases, provided by the present invention, can be applied include the following A to F.

A. Allergic disease-induced asthma or chronic or acute bronchitis
   a. Atopic predisposition-induced asthma or chronic or acute bronchitis
   b. Aspirin-containing drug-induced asthma or chronic or acute bronchitis
   c. Occupation-induced asthma or chronic or acute bronchitis
   d. Movement-induced asthma or chronic or acute bronchitis
   e. Other extrinsic stimulus-induced asthma or chronic or acute bronchitis
B. Non-allergic disease-induced asthma or chronic or acute bronchitis, infectious disease-induced asthma or chronic or acute bronchitis (extrinsic and intrinsic)
C. Respiration disorder-induced asthma or chronic or acute bronchitis
   a. Asthma or chronic or acute bronchitis induced by respiration disorder caused by autonomic imbalance
   b. Respiratory system disease-induced asthma or chronic or acute bronchitis
D. Asthma or chronic or acute bronchitis induced by respiratory tract inflammation caused by various diseases (e.g., diseases shown in C).
E. Respiratory tract diseases induced by inflammation and disorder of respiratory tract or bronchial tubes caused by the inhalation of respiratory tract- or bronchial tubes-impairing substances such as acids or organic solvents or by the inhalation of hot air.
F. Other respiratory system disease-induced respiratory tract diseases.

The effective dose of the preparation of the therapy of respiratory tract diseases, provided by the present invention, for a human being cannot be determined since it differs depending upon diseases to which the preparation should be applied, the graveness of respiratory tract diseases and the age and health condition of a patient. For the therapy of asthma, chronic bronchitis and acute bronchitis, however, the effective dose is generally in the range of 0.1 μg to 10 mg/diseased part. In administration route, in general, the preparation of the present invention can be administered widely to a diseased part by inhalation, while it may be directly administered to a diseased part if it can be directly applied or injected thereto. When topical administration is difficult, it may be systemically administered, such as orally or intravenously.

The preparation for the therapy of respiratory tract diseases, provided by the present invention, may be applied to the therapy of respiratory tract diseases of warm-blooded animals such as farm animals, pets and wild but raised animals. In this case, bovine bFGF and/or its homologues may be used, and the preparation form and dose thereof are as those specified concerning the preparation for a human being.

The activities and effects of the preparation for the therapy of respiratory tract diseases, provided by the present invention, will be explained hereinafter with reference to Examples.

[Example 1]—Cell Proliferation Promotion Activity of bFGF for Subcultured Strain of Epithelial Cells of Felin Bronchial Tubes AK-D A subcultured strain of epithelial cells of felin bronchial tubes AK-D (ATCC CCL-150) was subcultured in a Ham·F-12K (10% FCS) cell culture medium (supplied by Flow Laboratories), and 45th-generation cells were used in a test. Human bFGF (obtained by genetic recombination) in an amount of 0.1 to 10 ng/ml was added to the Ham·F-12K containing 10% FCS to prepare suspensions each containing $10^5$ cells/ml of AK-D, and 100 μl of each suspension was sown in 96-well culture plate (supplied by Falcon). Then, AK-D was cultured in a carbonic acid gas constant-temperature chamber. Each group included three examples. The day on which the culturing was started was taken as "0th" day, and the bFGF was measured for its proliferation capability on first, second and third days. The measurement was carried out according to "MTT assay" ("Igakuno Ayumi", vol. 128, No. 11, pages 733–735, 1984). That is, 10 μl of a solution containing 5 mg/ml of MTT (solution of 3-(4,5-dimethyl-2-thiazolyl)-2,5-diphenyl-2H-tetrazolium·bromide in PBS) was added to each well, and the AK-D was cultured for 6 hours. Then, 100 μl of a 0.04 N hydrochloric acid-isopropyl alcohol solution was added, and the mixtures were fully stirred and then measured for absorbance at a main wavelength of 540 nm and a reference wavelength of 690 nm with a spectrophotometer. FIG. 1 shows the results.

As FIG. 1 clearly shows, the bFGF exhibited AK-D cells proliferation promotion activity depending upon its doses in the range of 0.1 to 10 ng/ml. Further, the cell proliferation promotion activity was particularly remarkable on the second day, and FIG. 2 therefore shows the cell proliferation promotion activity on the 2nd day.

Figure 2:
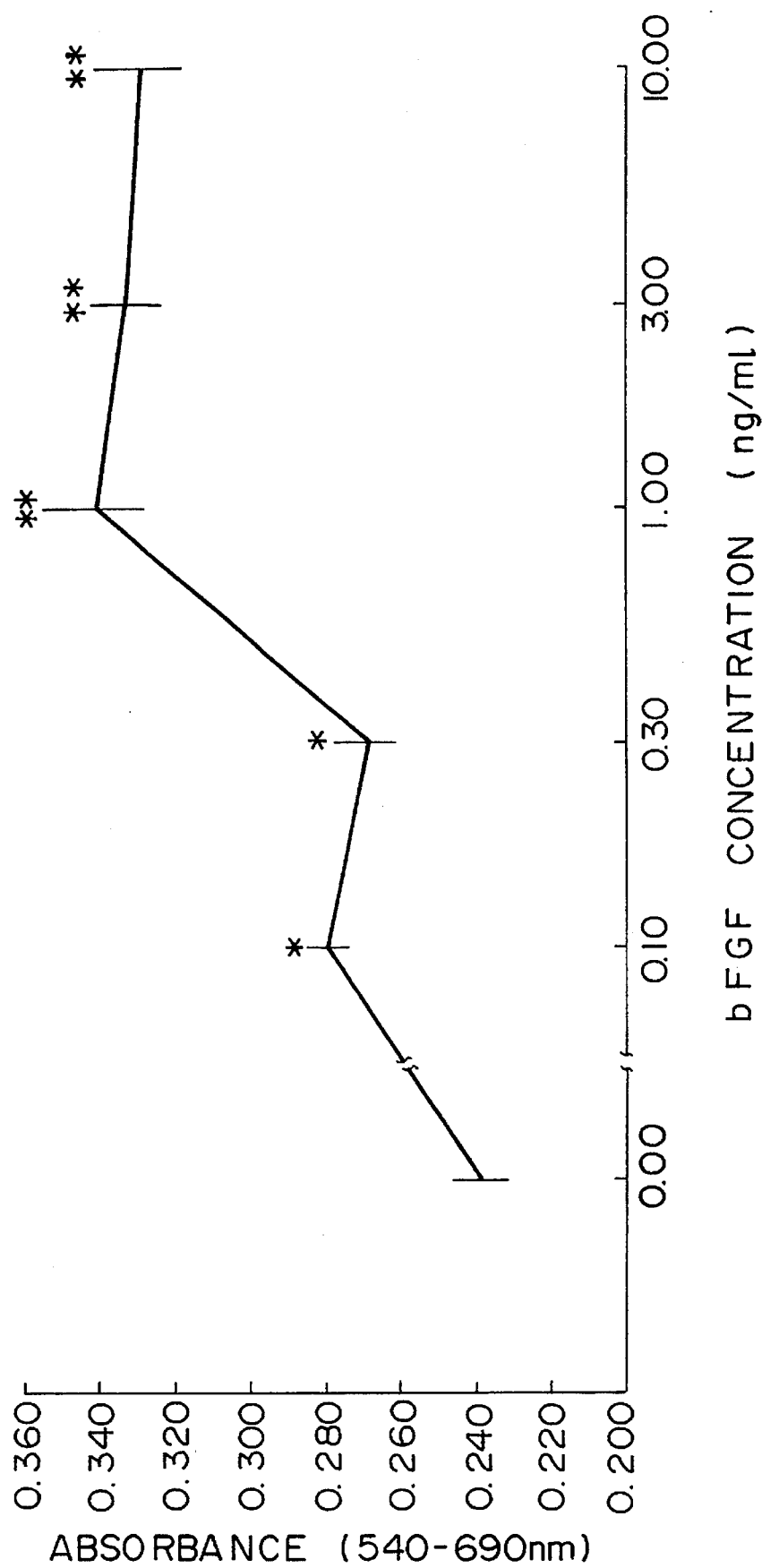
FIG. 2 is a graph showing the activity of bFGF for the proliferation promotion on a second day in Example 1 (in which * indicates that the assay result is $p<0.05$ and ** indicates that the assay result is $p<0.01$).

As shown in FIG. 2, the bFGF started to exhibit the significant AK-D cell proliferation promotion activity when used in a dose of 0.1 ng/ml, and this activity nearly arrived a plateau in a dose of 1 ng/ml.

Figure 3:
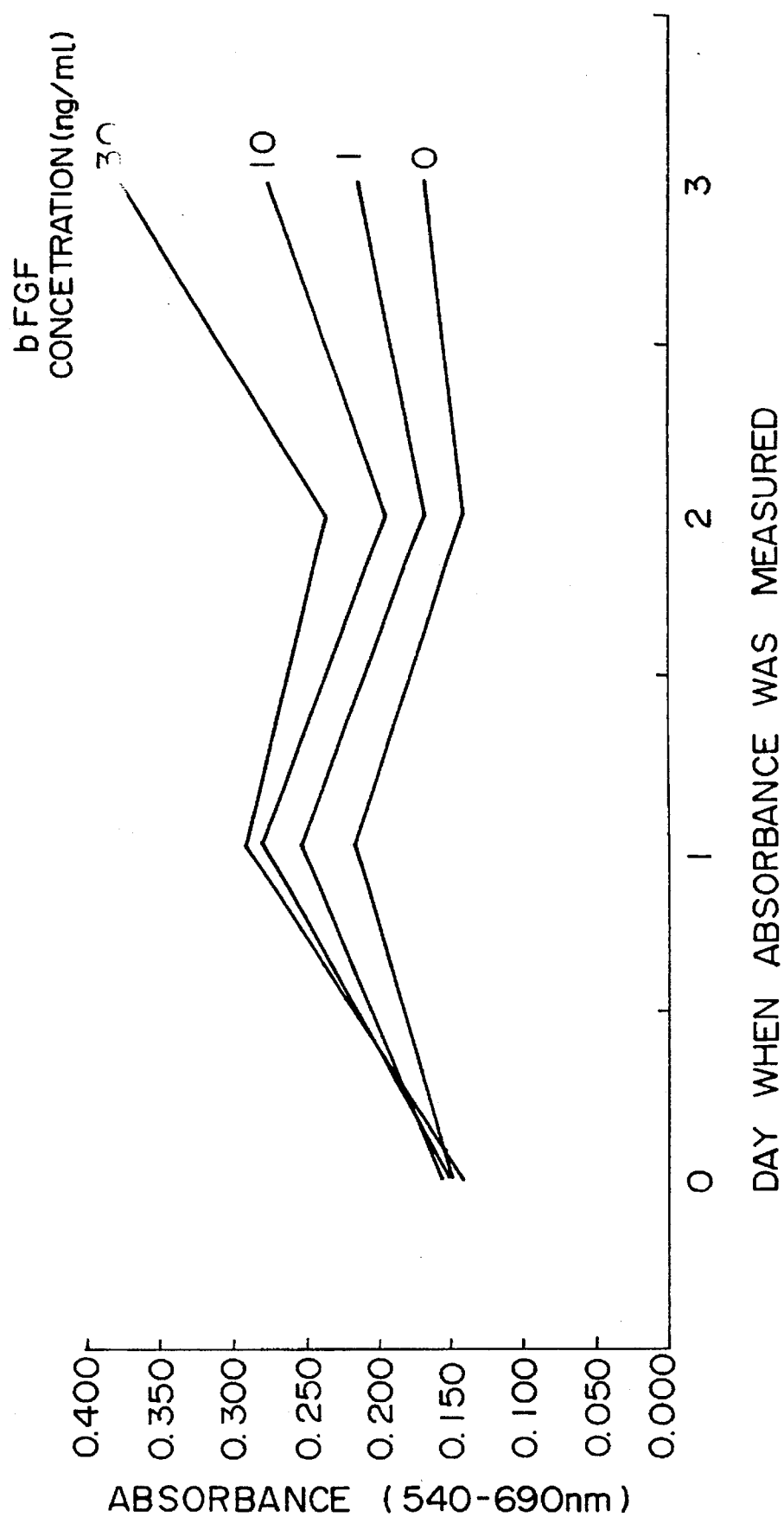
FIG. 3 is a graph showing the activity of bFGF for the cell proliferation from AK-D subconfluent in Example 2 to be described later.

[Example 2]—Cell Proliferation Promotion Activity of bFGF for Subcultured Strain of Epithelial Cells of Felin Bronchial Tubes AK-D A subcultured strain of epithelial cells of felin bronchial tubes AK-D was subcultured in a Ham·F-12K (10% FCS) cell culture medium, and 45th-generation cells were used in a test. A suspension of $10^5$ cells/ml of AK-D in the Ham·F-12K containing 10 % FCS was sown in a 96-well culture plate in an amount of 100 μl/well, and the AK-D was cultured in a carbonic acid gas constant-temperature chamber. The AK-D became subconfluent in four days after the culturing was started. The culture media in these subconfluent wells was replaced with F-12K containing no FCS, and 0.3 to 30 ng/ml of Human bFGF (obtained by genetic recombination) was added. Then, AK-D was further cultured in a carbonic acid gas constant-temperature chamber. Each group included three examples. The day on which this culturing was started was taken as "0th" day, and the bFGF was measured for its proliferation capability on first, second and third days. The measurement was carried out according to the "MTT assay". That is, 10 μl of a solution containing 5 mg/ml of MTT (solution of 3-(4,5-dimethyl-2-thiazolyl)-2,5-diphenyl-2H-tetrazolium·bromide in PBS) was added to each well, and the AK-D was cultured for 6 hours. Then, 100 μl of a 0.04N hydrochloric acid-isopropyl alcohol solution was added, and the mixtures were fully stirred and then measured for absorbance at a main wavelength of 540 nm and a reference wavelength of 690 nm with a spectrophotometer. FIG. 3 shows the results.

As shown in FIG. 3, no cell proliferation from the subconfluent was observed in a control group, while groups to which the bFGF had been administered showed the proliferation of AK-D cells depending upon its doses.

Figure 4:
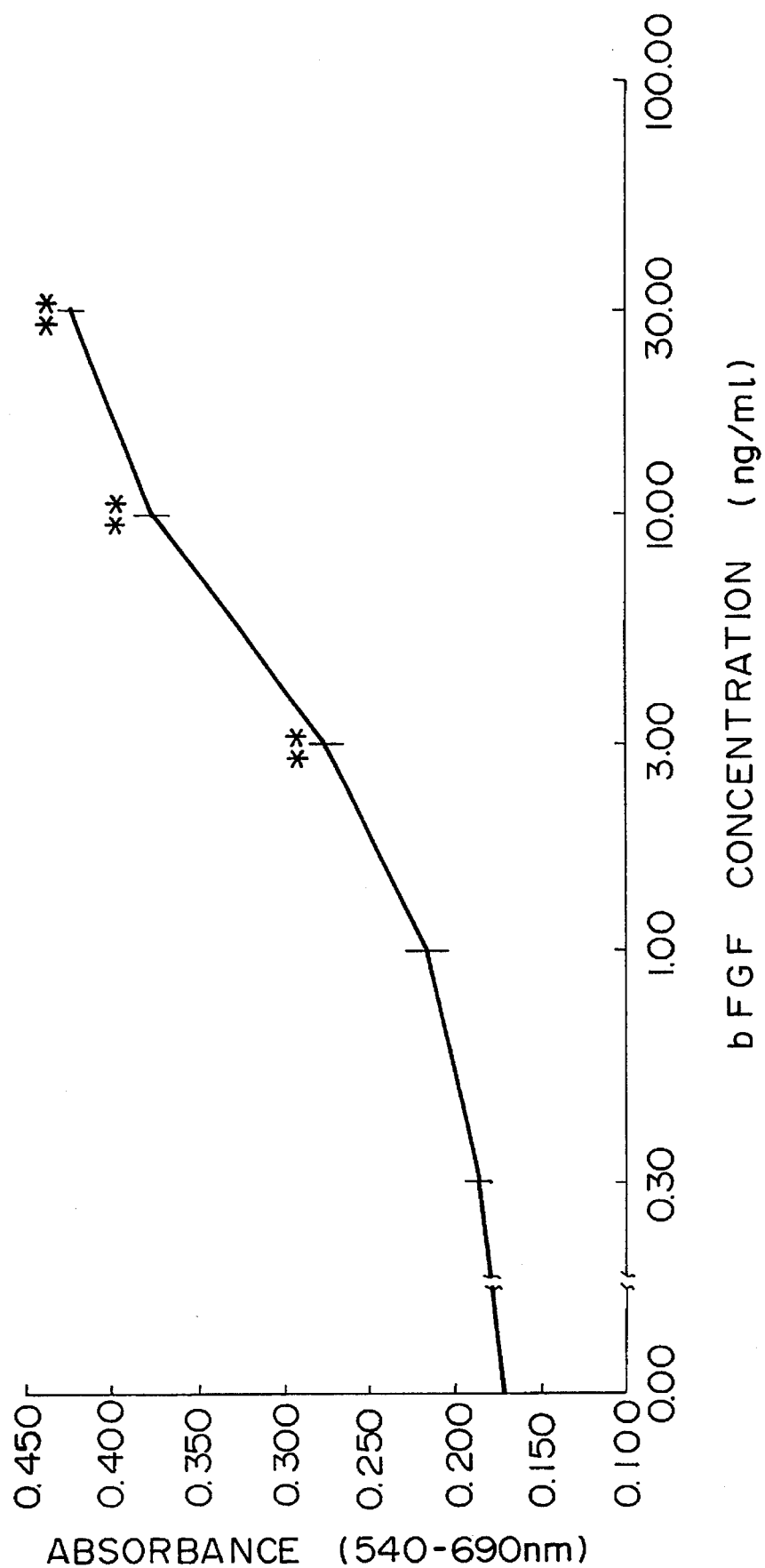
FIG. 4 is a graph showing the activity of bFGF for the proliferation promotion on a third day in Example 2 (in which ** indicates that the assay result is $p<0.01$).

FIG. 4 shows the cell proliferation activities on the third day. As shown in FIG. 4, the bFGF started to exhibit the significant cell proliferation promotion activity when used in a dose of 3 ng/ml.

As explained above, the present invention can provide a novel preparation for the therapy of respiratory tract diseases, which can treat that portion of a respiratory tract or bronchial tube impaired by various respiratory tract diseases, particularly inflammation, where the epithelial cells are impaired or peeled, and a method for the therapy of respiratory tract diseases using the same.

We claim:

1. A method for the treatment of asthma or bronchitis comprising administering to the diseased part of the respiratory tract an effective amount of at least one member selected from the group consisting of: basic fibroblast growth factor (bFGF) consisting of 146 amino acids, 157 amino acids, 155 amino acids, 147 amino acids, wherein the 147 amino acid form includes an N-terminal methionine, and a bFGF consisting of 146 amino acids wherein $Cys^{69}$ and $Cys^{87}$ are replaced by serine, to a warm-blooded animal in need thereof and wherein the bFGF is human or bovine.

2. A method according to claim 1, wherein the compound administered is human bFGF.

3. A method according to claim 1, wherein the warm-blooded animal is a human.

* * * * *

UNITED STATES PATENT AND TRADEMARK OFFICE
CERTIFICATE OF CORRECTION

PATENT NO. : 5,514,652
DATED : May 7, 1996
INVENTOR(S) : MITSURU WATANUKI ET AL.

It is certified that error appears in the above-indentified patent and that said Letters Patent is hereby corrected as shown below:

Column 8, line 1 (claim 1, line 5) change "157" to ---154---

Signed and Sealed this

Fourth Day of March, 1997

Attest:

BRUCE LEHMAN

*Attesting Officer*       *Commissioner of Patents and Trademarks*